United States Patent [19]
Inman et al.

[11] Patent Number: 5,747,527
[45] Date of Patent: May 5, 1998

[54] FURANOEREMOPHILANE AND EREMOPHILANOLIDE SESQUITERPENES FOR TREATMENT OF DIABETES

[75] Inventors: Wayne D. Inman, Belmont; Steven Row King, Moss Beach; Joseph L. Evans, San Francisco; Jian Luo, Brisbane, all of Calif.

[73] Assignee: Shaman Pharmaceuticals, Inc., South San Francisco, Calif.

[21] Appl. No.: 479,049

[22] Filed: Jun. 6, 1995

[51] Int. Cl.$^6$ .......................... A61K 31/35; A61K 31/355
[52] U.S. Cl. .............................................. 514/453; 514/468
[58] Field of Search .................................... 514/453, 468

[56] References Cited

PUBLICATIONS

Bohlmann et al, 1979, "Neu furanoeremophilane und weitere inhaltsstoffe aus sudafrikanischen senecio–arten", Phytochemistry 18:79–93.

Bye, Jr., 1986, "Medicinal plants of the Sierra Madre: Comparative study of Tarahumara and Mexican market plants", Economic Botany 40:103–124.

Hegnauer, 1989, *Chemotaxonome Der Pflanzen* (Birkhauser Verlag, Boston) pp. 280–281.

Huxtable, 1983, "Herbs along the western Mexican–American border", Proc. West. Pharmacol. Soc. 26:185–191.

Jankowski et al., 1984, "The unambiguous assignment of $^1$H and $^{13}$C signals in the NMR spectrum of cacalone acetate", Proc. Indian Acad. Sci. (Chem. Sci.) 93:1317–1321.

Krasovskaya et al., 1990, "Natural antioxidants: Furanoeremophilanes from Cacalia roots", Khimiya Prirodnykh Soedinenii 5:643–646.

Kuroyanagi et al., 1985, "Furanoeremophilane–type sesquiterpenes from Cacalia adenostyloides", Chem. Pharm. Bull. 33:4792–4797.

Lotina–Hennsen et al., 1991, "Inhibition of oxygen evolution by cacalol and its derivatives", Z. Naturforsch 46:777–780.

Manuel et al., 1992, "Actividad antimicrobiana del cacalol y sus derivados", Rev. Latinoamer. Quim. 23/1 and 22/4:14–17.

Marles and Farnsworth, 1994, "Plants as sources of antidiabetic agents", *Economic and Medicinal Plant Research* (Academic Press, New York) pp. 149–187.

Omura et al., 1978, "The sesquiterpenes of Cacalia species: 8–oxocacalol and the stereochemistry of cacalone epimers", Chem. Lett. pp. 1257–1260.

Perez et al., "A study of the hypoglucemic effect of some Mexican plants", J. Ethnopharmacology 12:253–262 (1984).

Rojas et al., 1994, "Phytochemistry of medicinal plants", 1994 Annual Meeting of the Phytochemical Society of North America (Poster 62).

Roman–Ramos et al., 1992, "Hypoglycermic activity of some antidiabetic plants", Archives Med. Res. 23:105–109.

Roman–Ramos et al., 1991, "Experimental study of the hypoglycemic effect some antidiabetic plants", Arch. Inves. Med. (Mex.) 22:87–93.

Romo and Nathan, 1964, "The constituents of Cacalea decomposita", Tetrahedron 20:2331–2337.

Soriano–Garcia et al., 1988, "Structure and stereochemistry of cacalone acetate, a sesquiterpene", Acta Cryst. 44:1092–1094.

Steinegger and Hansel, 1988, *Lehrbuch der Pharmakognosie und Phytopharmazie* (Springer–Verlag, New York).

Terabe et al., 1978 "Absolute stereochemistry of cacalol", Bull. Chem. Soc. Japan 51:661–662.

Winkelman, 1989, "Ethnobotanical treatments of diabetes in Baja California Norte", Medical Anthropology 11:255–268.

Gerald Sullivan, "Detection of Pyrrolizidine–type Alkaloids in Matarique (Cacalia Decomposita)", Vet. Hum. Toxicol. 23(1) (Feb. 1981).

Anaya et al., "Phytotoxicity of Cacalol and Some Derivatives Obtained from the Roots of *Psacalium decompositum* (A. Gray) H. Rob. & Brettell (Asteraceae), Matarique or Maturin", J. Chem. Ecology 22(3):393–403 (1996).

*Primary Examiner*—Amelia Averill Owens
*Attorney, Agent, or Firm*—Pennie & Edmonds

[57] ABSTRACT

Novel hypoglycemically active eremophilanolide sesquiterpenes which can be isolated from *Psacalium spp.*, processes for obtaining the novel eremophilanolide sesquiterpenes and methods for their use as hypoglycemic agents, for example, in the treatment of diabetes are described. Further described is the use of epicacalone, cacalone, cacalol or dimaturin as hypoglycemic agents, for example, in the treatment of diabetes. In a preferred embodiment, the hypoglycemically active compounds are obtained from the roots of *Psacalium decompositum*. As agents for the treatment of diabetes, the hypoglycemically active compounds of the present inventions are useful for treating insulin-dependent (type I) and/or non-insulin-dependent (type II) diabetes.

13 Claims, 4 Drawing Sheets

FURANOEREMOPHILANE AND EREMOPHILANOLIDE SESQUITERPENES FOR TREATMENT OF DIABETES

1. FIELD OF THE INVENTION

The present invention relates to a series of furanoeremophilane and eremophilanolide sesquiterpenes, including novel eremophilanolides, which exhibit hypoglycemic and/or anti-diabetic activity in mammals, and provides methods and compositions for their use, as well as processes for their isolation.

2. BACKGROUND OF THE INVENTION

2.1 Uses of *Psacalium spp.*

Plants of the genus Psacalium (syn. Senecio), e.g. *P. peltatum* and *P. decompositum* (family Asteraceae, tribus Senecioneae) are used in the United States, Mexico and other parts of Central America, usually in the form of aqueous decoctions, for the treatment of a variety of ailments including diabetes, (e.g. R. J. Huxtable, *Proc. West. Pharmacol. Soc.* 26, 185 (1983); R. M. Perez, G. A. Ocegueda, J. L. Munoz, J. G. Avila, W. W. Morrow, *J. Ethnopharmacol.* 12, 253 (1984); R. A. Bye jr., *Econ. Bot.* 40, 103 (1986); M. Winkelman, *Med. Anthropol.* 11, 255 (1989)). *P. decompositum* is used by the following indigenous groups in Mexico: the Tarahumara indigenous group of Sonora state use a root decoction to treat diabetes mellitus and rheumatism (Atlas do las Plantes Traditionales de Mexicana, vol. 111, p. 185, 1994); the Yaqui indigenous group of the Sonora state treat rheumatic pain in joints, gout, and skin ulcerations (Herrera, A. Instituto Medico Nacional Vol. IX, 1907); the Pima indigenous group of Sonora and Chihuahua states use a warm or hot water extraction to treat colds, weak people with poor appetites, and to strengthen blood (Flora Medicinale Indigena de Mexico, vol. 1, INI, p. 124, 1994). Hypoglycemic effects of aqueous and methanolic extracts of *P. peltatum* were experimentally determined in mice (L. Sanchez, R. Roman, F. Alarcon, J. L. Flores, R. Soto, 1994 Annual Meeting of the Phytochemical Society of North America, Poster #63) and in normal and alloxan-treated rabbits (R. Roman-Ramos, J. L. Flores-Saenz, G. Partida-Hernandez, A. Lara-Lemus, F. Alarcon-Aguilar, *Arch. Invest. Med.* (Mex.) 22, 87 (1991); ibid. 23, 105 (1992)), whereby it was found that the effect was most pronounced in normal, non-diabetic animals.

Asteraceae plants of the tribus Senecioneae are rich in pyrrolizidine alkaloids (R. Hegnauer, "Chemotaxonomie der Pflanzen", Vol. VIII, pp. 280–281, Birkhäuser Verlag, Basel, 1989, and references cited therein), which because of their pronounced hepatotoxicity, have been suspected to be the hypoglycemic agents in these plants (eg. R. J. Marles and N. R. Farnsworth in *"Econ. Med. Plant Res."*, Vol. VI, 149 (1994); E. Steinegger, R. Hänsel "Lehrbuch der Pharmakognosie und Phytotherapie", p.521, Springer Verlag 1988)).

While the presence of these compounds in *P. decompositum* has been verified by the inventors, no such compounds are present in any of the active extracts of this invention, nor are these compounds structurally in any way related to the antidiabetic compounds isolated from these extracts and claimed herein.

Certain members of a class of furanoeremophilanes, not including, however, the novel antidiabetic compounds of the present invention have been isolated from members of the Senecioneae tribe (eg. F. Bohlmann, C. Zdero, D. Berger, A. Suwita, P. Mahanta, C. Jeffrey, *Phytochemistry* 18, 79 (1979) and references cited therein). The furanoeremophilane skeleton is distinguished from other sesquiterpenes by the presence of the furano and decalin fused ring system along with two methyl groups at C-3 and C-5, and another methyl group located at either C-4 or C-4a.

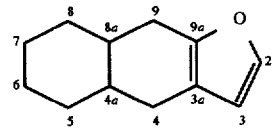

Oxidation of the furan to a lactone leads to the eremophilanolide skeletal type.

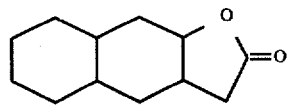

2.2 Compounds Isolated Previously from *Psacalium spp.*

In the furanoeremophilane class, compounds such as cacalol and cacalone have been described. Cacalol and cacalone were originally isolated from *Cacalia decomposita* ((syn. *Parasenecio decomp.*) (J. Romo and P. Joseph-Nathan *Tetrahedron* 20, 2331 (1964)); after many revisions the correct structure for cacalone was proposed based upon intensive n.m.r. analyses (K. Jankowski, E. Diaz, F. Yuste *Proc. Indian Acad. Sci.* (*Chem. Sci.*) 93, 1317 (1984)) and verified by X-ray crystallography (M. Soriano-Garcia, F. Walls, H. Barrios, R. Sanchez-Obregon, B. Ortiz, E. Diaz, R. A. Toscano, F. Yuste *Acta Cryst.* C44, 1092 (1988), and references cited therein); the absolute configuration for cacalol was determined to be 5S (M. Terabe, M. Tada, T. Takahashi *Bull. Chem. Soc. Jpn.* 51, 661 (1978)). The structures of epicacalone and adenostylide from *Cacalia adenostyloides* were also determined previously (K. Omura, M. Nakanishi, K. Takai, K. Naya *Chem. Let.* 1978, 1257; M. Kuroyanagi, H. Naito, T. Noro, A. Ueno, S. Fukushima *Chem. Pharm. Bull.* 33, 4792 (1985)).

Cacalol and its acetate show pronounced antioxidant activity (N. P. Krasovskaya, N. I. Kulesh, V. A. Denisenko *Chem. Nat. Comp.* 25, 545 (1990)) and inhibit electron transport and phosphorylation in plant chloroplasts (B. Lotina-Hennsen, J. L. Roque-Resendiz, M. Jimenez, M. Aguilar Z. *Naturforsch.* Ser. C 46, 777 (1991)); the former effect was weaker for cacalone. Cacalol and its acetyl- and acetate derivatives show weak antibacterial and antifungal effects in agar seeded assays (M. Jimenez, C. Lozano, J. Valdes, J. Leon, G. Alacon, B. Sveshtarova *Rev. Latinoamer. Quim.* 23/1 and 22/4, 14 (1992)).

To the best of the inventors knowledge, no prior study has described any hypoglycemic activity for any of the furanoeremophilane or eremophilanolide compounds of the present invention, nor was there any suggestion in the prior art that the compounds of the present invention could be useful as antidiabetic agents.

Citation or identification of any reference in Section 2 of this application shall not be construed as an admission that such reference is available as prior art to the present invention.

3. SUMMARY OF THE INVENTION

The present invention provides novel eremophilanolides, as well as pharmaceutically acceptable salts thereof, having hypoglycemic activity, compositions comprising the novel eremophilanolides of the present invention, as well as methods for their use. In addition, the present invention provides compositions comprising furanoeremophilanes and methods for their use as hypoglycemic agents.

Particularly, the present invention provides novel eremophilanolides having the structure of compound 3:

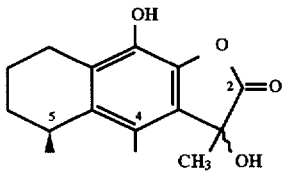

and pharmaceutically acceptable salts thereof for use as hypoglycemic agents.

The invention further encompasses a method for using epicacalone, cacalone, compound 3, cacalol, dimaturin, pharmaceutically acceptable salts thereof or mixtures thereof as a hypoglycemic agent.

Still further, the invention encompasses compositions comprising epicacalone, cacalone, compound 3, cacalol, dimaturin, pharmaceutically acceptable salts thereof or mixtures thereof for use as a hypoglycemic agent in mammals. Such compositions optionally contain pharmaceutically acceptable carriers or vehicles and optionally other hypoglycemic agents.

Still further, the invention encompasses methods for reducing blood glucose in a mammal, comprising administering to a mammal in need of such blood glucose reduction, an effective amount of an extract from Psacalium spp. in which said extract was obtained by a process which comprised:

(a) washing plant material from Psacalium spp. with a non-polar organic solvent to obtain an organic solution of hypoglycemically active compounds;

(b) concentrating the organic solution to obtain an enriched mixture of hypoglycemically active compounds;

(c) washing the enriched mixture of hypoglycemically active compounds with a biphasic mixture of a polar solvent and a hydrocarbon solvent to obtain a bioactive polar solution, wherein said polar solvent and said bioactive polar solution are immiscible in said hydrocarbon solvent; and (d) concentrating said bioactive polar solution to obtain an extract useful as a hypoglycemic agent.

Still further, the invention encompases methods for treatment of diabetes mellitus comprising administering to a mammal suffering from diabetes mellitus a therapeutically active amount of an extract from Psacalium spp. in which said extract was obtained by a process which comprised:

(a) washing plant material from Psacalium spp. with a non-polar organic solvent to obtain an organic solution of hypoglycemically active compounds;

(b) concentrating the organic solution to obtain an enriched mixture of hypoglycemically active compounds;

(c) washing the enriched mixture of hypoglycemically active compounds with a biphasic mixture of a polar solvent and a hydrocarbon solvent to obtain a bioactive polar solution, wherein said polar solvent and said bioactive polar solution are immiscible in said hydrocarbon solvent; and (d) concentrating said bioactive polar solution to obtain an extract useful as a hypoglycemic agent.

Still further, the invention includes pharmaceutical compositions for use as a hypoglycemic agent in mammals, comprising a therapeutically effective amount of an extract from Psacalium spp. in which said extract was obtained by a process which comprised:

(a) washing plant material from Psacalium spp. with a non-polar organic solvent to obtain an organic solution of hypoglycemically active compounds;

(b) concentrating the organic solution to obtain an enriched mixture of hypoglycemically active compounds;

(c) washing the enriched mixture of hypoglycemically active compounds with a biphasic mixture of a polar solvent and a hydrocarbon solvent to obtain a bioactive polar solution, wherein said polar solvent and said bioactive polar solution are immiscible in said hydrocarbon solvent; and (d) concentrating said bioactive polar solution to obtain an extract useful as a hypoglycemic agent.

The present invention may be understood more fully by reference to the following figures, detailed description and illustrative examples which are intended to exemplify non-limiting embodiments of the invention.

4. DESCRIPTION OF THE FIGURES

FIG. 1 is a bar graph showing the plasma glucose levels (mg/dl) of diabetic mice treated with varying doses of cacalol. Animals were dosed at 0 and 24 hours. All data points $N=8$ except for $a=7$, $b=4$ and $c=3$. $*P<0.05$; $P<0.01$; $*P<0.001$ (analysis of variance (ANOVA), one factor).

FIG. 2 is a bar graph showing the plasma glucose levels (mg/dl) of diabetic mice treated with epicacalone, cacalone, compound 3 and cacalol. Animals were dosed at 0 hour. All data points $N=8$ except for $a=7$. $*P<0.05$; $P<0.01$; $*P<0.001$ (ANOVA, one factor).

Figure 1:
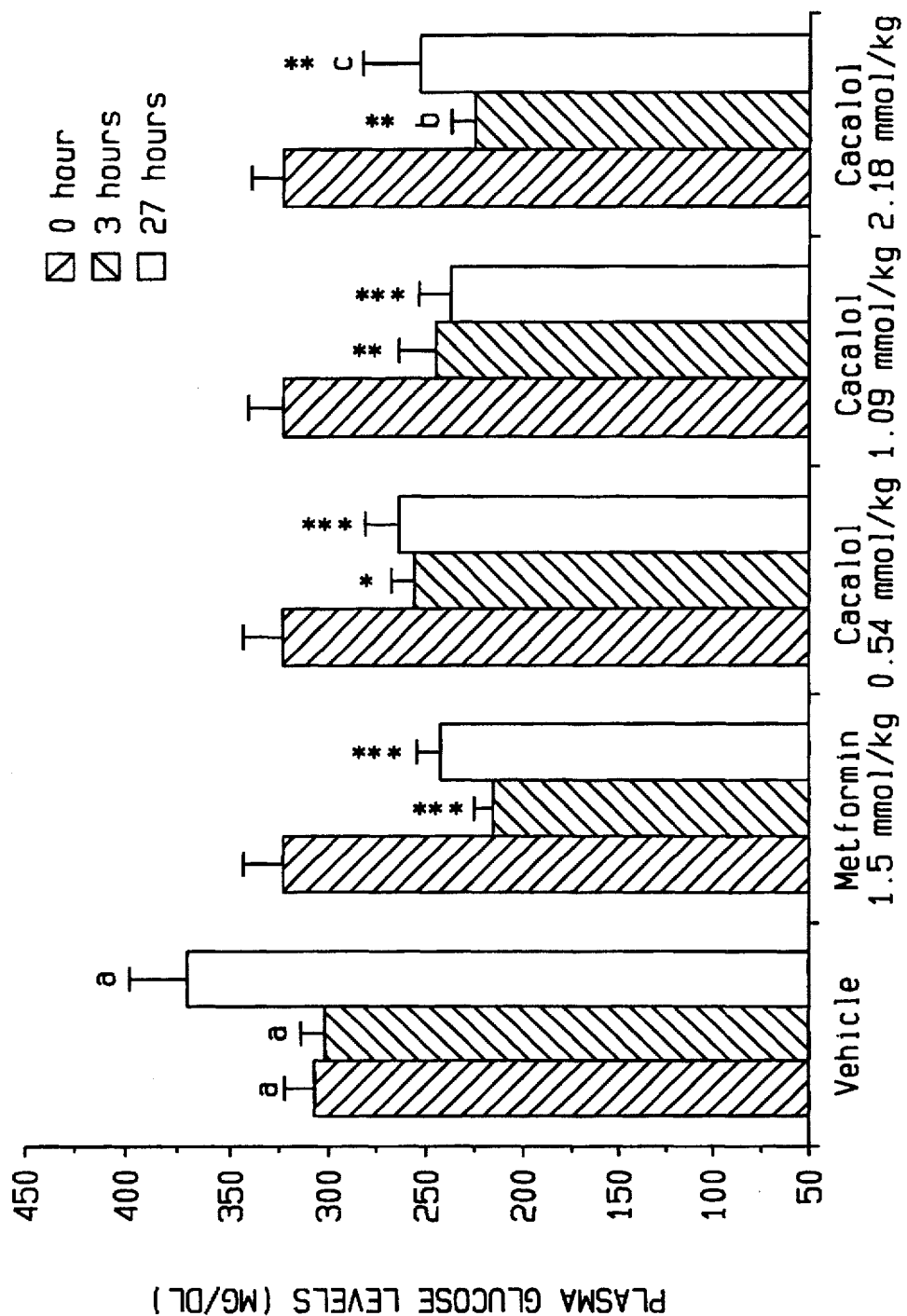

5. DETAILED DESCRIPTION OF THE INVENTION 5.1 Eremophilanolide Hypoglycemic Agents The novel eremophilanolides of the present invention useful as hypoglycemic agents have the structure of compound 3:

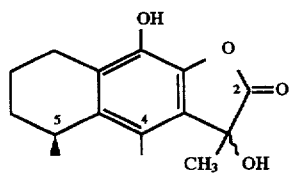

It is to be understood that the invention encompasses both epimers of compound 3, namely compound 3a:

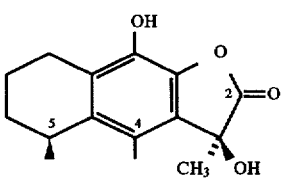

and compound 3b:

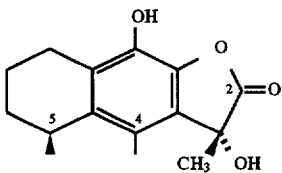

Compound 3 or epimers 3a or 3b can be obtained via extraction from *Psacalium spp.*, preferably *P. decompositum* (see Section 5.2, below) or from conventional organic synthesis using methods known to those of skill in the art.

5.2 Processes for Isolating Furanoeremophilane and Eremophilanolide Hypoglycemic Agents The furanoeremophilane and eremophilanolide sesquiterpenes useful as hypoglycemic agents can be isolated from *Psacalium spp.*, preferably *P. decompositum*, using the illustrative methods described below or other standard extraction techniques known to those of ordinary skill in the art.

5.2.1 Isolation using Aqueous and Alcoholic Solvent Extraction

Plant material from *Psacalium spp.* preferably *P. decompositum*, is extracted with water to extract the hypoglycemically active compounds therefrom. By "plant material" is meant any part of the plant, such as leaves, flowers, roots and stems. The plant material may optionally be shredded, ground, macerated, or otherwise treated to reduce its surface area prior to extraction. The water temperature can range from 22° C. to 100° C., preferably from 40° C. to 60° C. Most preferably, the water temperature is 55° C. The water extraction can be run for several minutes to several days, preferably for one day.

After the extraction is complete, the aqueous mixture of plant material is filtered to remove undesired solids therefrom and to afford a filtrate containing hypoglycemically active compounds. If the temperature of the water used in the extraction is greater than room temperature, the water containing the hypoglycemically active compounds can be optionally cooled to room temperature prior to filtration. The resulting filtrate is concentrated, preferably in vacuo, to afford an amorphous extract.

The amorphous extract is added to a cold solution of aqueous organic alcohol so as to precipitate insoluble impurities therefrom. By "aqueous organic alcohol" is meant a solution of water and an organic alcohol such as methanol, ethanol, isopropanol, sec-butanol and the like, wherein the ratio of water to organic alcohol ranges from 5:95 to 95:5 volume/volume (v/v), preferably from 5:95 to 20:80 v/v. Most preferably, the ratio of water to organic alcohol is from 10:90 to 20:80 v/v and the organic alcohol is isopropanol. By "cold" is meant that the temperature of the aqueous organic alcohol is below room temperature but above the freezing point of the aqueous organic alcohol solution. Preferably, the temperature of the aqueous organic alcohol solution is between 0° and 10° C.

Following addition of the amorphous extract to the cold aqueous organic alcohol solution, the resulting mixture is allowed to stand at a temperature below room temperature but above the freezing point of the aqueous organic alcohol solution to allow for the formation of solid impurity. The length of time necessary for formation of the solid impurity depends upon such factors as the ratio of water to organic alcohol solution, the temperature of the aqueous organic alcohol solution, the percentage of solid impurity, etc. Preferably, the mixture of amorphous extract and aqueous organic alcohol is allowed to stand from 1 to 24 hours. The filtrate containing the hypoglycemically active compounds is separated from the solid impurity by filtration or decantation to afford a supernatant containing the hypoglycemically active compounds. The supernatant is concentrated, preferably in vacuo, to afford an enriched bioactive material.

The enriched bioactive material is diluted with an organic solvent capable of dissolving the enriched bioactive material and the hypoglycemically active compounds therein and washed with an aqueous acidic solution to remove nitrogen-containing impurities, including but not limited to undesired alkaloids, therefrom. Suitable organic solvents are those which are immiscible in water and include ethyl acetate, diethyl ether, hexane, chloroform, carbon tetrachloride and preferably, dichloromethane (DCM). Suitable aqueous acidic solutions are dilute solutions of water and acids such as hydrochloric, nitric, sulfuric, acetic and citric. Preferably, the aqueous acidic solution is an aqueous solution of hydrochloric acid, most preferably 1N HCl. After the organic solution is washed with the aqueous acidic solution, the organic solution free from alkaloid impurities and containing the hypoglycemically active compounds is concentrated, preferably in vacuo, to afford a crude mixture of hypoglycemically active compounds epicacalone, cacalone and compound 3.

The crude mixture of hypoglycemically active compounds can be purified by recrystallization or chromatography, preferably high-performance liquid chromatography, to afford pure hypoglycemically active compounds. When high-performance liquid chromatography is used to separate the crude mixture into fractions containing pure hypoglycemically active compounds, the eluent solution is generally a mixture of water and a polar organic solvent miscible with water. Preferably, the eluent solution is a mixture of acetonitrile and water. Optionally, the resulting fractions may be repurified using high-performance liquid chromatography to obtain fractions of higher purity, using the same or preferably a slower elution flow rate.

5.2.2 Isolation using Non-Polar Orangic Solvent Extraction

In a preferred embodiment of the invention, plant material from *Psacalium spp.*, preferably *P. decompositum*, is washed with a non-polar organic solvent to extract hypoglycemically active furanoeremophilane or eremophilanolide compounds therefrom while leaving behind undesired alkaloid impurities in the plant material. The plant material may optionally be shredded, ground, macerated, or otherwise treated to reduce its surface area prior to washing. Suitable non-polar organic solvents useful in this regard include dichloromethane and mixtures of diethyl ether and hexane. When mixtures of diethyl ether and hexane are used, the ratio of diethyl ether to hexane is preferably 1:2. The preferred non-polar organic solvent is dichloromethane. After washing the plant material, the non-polar organic solvent containing the hypoglycemically active compounds is concentrated, optionally in vacuo, to afford an extract enriched in hypoglycemically active compounds.

The enriched extract is then diluted with a polar solvent and washed with a hydrocarbon solvent so as to remove non-polar organic impurities therefrom. Useful polar solvents include, but are not limited to, methanol, ethanol, isopropanol, acetone, 2-butanone, ethyl acetate, tetrahydrofuran, dimethylformamide, N-methylpyrrolidinone, dimethyl sulfoxide, water and mixtures thereof. It is important that the polar solvent be immiscible in the hydrocarbon solvent so as to form an effective biphasic partitioning system. Useful hydrocarbon solvents include benzene, toluene, pentane, hexane, heptane, higher ($>C_7$) alkanes and other hydrocarbon solvents, such as petroleum ether, immiscible in the polar solvent. Preferably, the hydrocarbon solvent is petroleum ether and the polar solvent is a mixture of ethanol and water. Most preferably, the polar solvent is 10% aqueous ethanol. After washing the enriched extract, the polar solvent phase is separated and then concentrated, optionally in vacuo, to afford a residue of bioactive material containing cacalol, dimaturin, compound 3, epicacalone and cacalone.

The bioactive material is purified by recrystallization or chromatography, preferably vacuum flash chromatography. When vacuum flash chromatography is used, the bioactive material is preferably pre-adsorbed onto silica gel which is then added to the top of a column of clean silica gel and eluted with standard organic solvent systems, preferably ethyl acetate/hexane. Preferably, the bioactive material is pre-adsorbed onto silica gel by dissolving the bioactive material in an organic solvent such as dichloromethane, adding silica gel to the dichloromethane solution of the hypoglycemically active compounds to afford a silica gel slurry and drying the silica gel, preferably in vacuo. The fractions obtained from the vacuum flash chromatography are concentrated, optionally in vacuo, to afford purified hypoglycemically active compounds. Preferably, the concentrated fractions are repurified using recrystallization or chromatography to afford pure cacalol, dimaturin, compound 3, epicacalone and cacalone. Repurification may be repeated several times or until the desired degree of compound purity is obtained.

5.3 Methods for use of Hypoglycemically Active Furanoeremophilane and Eremophilanolide Compounds Due to the potent hypoglycemic activity of the furanoeremophilane and eremophilanolide sesquiterpenes of the present invention, the furanoeremophilane or eremophilanolide compounds are advantageously useful in veterinary and human medicine for therapeutic treatment of diabetes mellitus. Additionally, the furanoeremophilane or eremophilanolide compounds can be advantageously used as hypoglycemic agents to reduce the blood glucose level in situations of acute stress such as experienced by animals or patients with hyperthermia, trauma, sepsis, and burns and undergoing general anesthesia. Hyperglycemia sometimes associated with severe head injury, cerebral thrombosis, encephalitis and heat stroke can also be therapeutically treated with these compounds. Additionally, the furanoeremophilane or eremophilanolide compounds are useful as hypoglycemic agents for rare congenital metabolic glycogen storage disease associated with hyperglycemia.

Although the present inventors do not wish to be limited to any particular mechanism of action to explain the hypoglycemic activity of the furanoeremophilane or eremophilanolide compounds of the present invention, it is envisaged that they may advantageously be useful for treatment of both insulin-dependent or type I diabetes (formerly termed juvenile-onset or ketosis-prone diabetes) and non-insulin-dependent or type II diabetes (formerly termed adult-onset, maturity-onset or nonketotic diabetes).

When administered to a mammal for veterinary use or to a human for clinical use, the furanoeremophilane or eremophilanolide compounds can be used alone, or may be combined with any physiologically acceptable carrier such as water, an aqueous solution, normal saline, or other physiologically acceptable excipient. In general, the dosage would range from about 10–1000 mg/kg/day, preferably about 10–250 mg/kg/day.

The furanoeremophilane or eremophilanolide compounds can be administered by a number of routes, including, but not limited to: orally, injection including, but not limited to intravenously, intraperitoneally, subcutaneously, intramuscularly, etc. The preferred route of administration is oral. Additionally, the furanoeremophilane or eremophilanolide compounds can be administered in conjunction with another hypoglycemic agent including such as insulin; a biguanide such as metformin or buformin; a sulfonylurea such as acetohexamide, chlorpropamide, tolazamide, tolbutamide, glyburide, glypizide or glyclazide; a thiazolidinedione such as troglitazone; an α-glycosidase inhibitor such as acarbose or miglatol; or a $\beta_3$-adrenoceptor agonist such as CL-316, 243, etc.

The furanoeremophilane or eremophilanolide compounds of the present invention can optionally be administered in an effective amount as pharmaceutically acceptable phenolate salts using counter ions such as sodium, potassium, lithium, calcium, magnesium, zinc and iron.

In addition, the furanoeremophilane or eremophilanolide compounds or pharmaceutically acceptable salts thereof can be used for research purposes, for example, to investigate the mechanism and activity of hypoglycemic agents.

5.4 Methods for Isolating and using Extracts of *Psacalium spp.*

Extracts of *Psacalium spp.* prepared using the methods described in Section 3, above, have hypoglycemic activity.

Due to the potent hypoglycemic activity of the extracts of *Pscalium spp.* of the present invention, the extracts of *Pscalium spp.* are advantageously useful in veterinary and human medicine for therapeutic treatment of diabetes mellitus. Additionally, the extracts of *Pscalium spp.* can be advantageously used as hypoglycemic agents to reduce the blood glucose level in situations of acute stress such as experienced by animals or patients with hyperthermia, trauma, sepsis, and burns and undergoing general anesthesia. Hyperglycemia sometimes associated with severe head injury, cerebral thrombosis, encephalitis and heat stroke can also be therapeutically treated with these compounds. Additionally, the extracts of *Pscalium spp.* are useful as hypoglycemic agents for rare congenital metabolic glycogen storage disease associated with hyperglycemia.

Although the present inventors do not wish to be limited to any particular mechanism of action to explain the hypoglycemic activity of the extracts of *Pscalium spp.* of the present invention, it is envisaged that they may advantageously be useful for treatment of both insulin-dependent or type I diabetes (formerly termed juvenile-onset or ketosis-prone diabetes) and non-insulin-dependent or type II diabetes (formerly termed adult-onset, maturity-onset or nonketotic diabetes).

When administered to a mammal for veterinary use or to a human for clinical use, the extracts of *Pscalium spp.* can be used alone, or may be combined with any physiologically acceptable carrier such as water, an aqueous solution, normal saline, or other physiologically acceptable excipient. In general, the dosage would range from about 10–1000 mg/kg/day, preferably about 10–250 mg/kg/day.

The extracts of *Pscalium spp.* can be administered by a number of routes, including, but not limited to: orally, injection including, but not limited to intravenously, intraperitoneally, subcutaneously, intramuscularly, etc. The preferred route of administration is oral. Additionally, the extracts of *Pscalium spp.* can be administered in conjunction with another hypoglycemic agent including such as insulin; a biguanide such as metformin or buformin; a sulfonylurea such as acetohexamide, chlorpropamide, tolazamide, tolbutamide, glyburide, glypizide or glyclazide; a thiazolidinedione such as troglitazone; an α-glycosidase inhibitor such as acarbose or miglatol; or a $\beta_3$-adrenoceptor agonist such as CL-316, 243, etc.

The extracts of *Pscalium spp.* of the present invention can optionally be administered in an effective amount as pharmaceutically acceptable phenolate salts using counter ions such as sodium, potassium, lithium, calcium, magnesium, zinc and iron.

In addition, the extracts of *Pscalium spp.* or pharmaceutically acceptable salts thereof can be used for research purposes, for example, to investigate the mechanism and activity of hypoglycemic agents.

The following series of Examples are presented by way of illustration and not by way of limitation on the scope of the invention.

6. EXAMPLE: ISOLATION AND CHARACTERIZATION OF FURANOEREMOPHILANE AND EREMOPHILANOLIDE SESQUITERPENES

6.1 Materials and Methods

Analytical high performance liquid chromatography (HPLC) was performed on a Hitachi Model D-6500 Chromatography Data Station equipped with a L-6200A pump, AS-2000 autosampler, L-4500 A diode array detector and a Sedex 55 light scattering detector connected in parallel. Columns used in analytical HPLC were an ODS-AQ (YMC Inc.), 4×50 mm (3 µm), and phenyl (YMC Inc.), 4×50 mm (3 µm). Semi-preparative HPLC was performed on a Hitachi Model D-6500 Chromatography Data Station equipped with a Waters 600 pump controller, L-4500 A diode array detector, and a L-5200 Hitachi fraction collector. Columns used in semi-preparative HPLC were a PRP-1 (Hamilton), 20×250 mm (10 µm) column, ODS-AQ (YMC Inc.), 20×150 mm (5 µm) equipped with a 20×50 mm guard column, and a phenyl (YMC Inc.), 20×250 mm (5 µm) column. Preparative HPLC chromatography was performed with a Rainin Dynamax HPLC system equipped with a Dynamax Diode Array Detector (Model PDA-1), solvent delivery pumps (Model SD-1), and interfaced with Dynamax PC HPLC Data System. Chromatographic columns used were a Hamilton PRP-1, 50×250 mm or Primesphere C18 HC (10 µm) 50×250 mm with a pre-column 50×30 mm (both columns obtained from Phenomenex, Torrance, Calif.). All chromatographic runs were performed at ambient temperature. HPLC grade or ACS grade solvents were used without further purification.

Nuclear magnetic resonance (NMR) spectra were recorded on a Varian Unity Plus 400 or a Varian Unity 400 spectrometer. All NMR spectra of compounds were recorded in deuterated chloroform. One and two-dimensional NMR experiments, including Distortionless Enhancement Polarization Transfer (DEPT), H-H Correlation Spectroscopy (COSY), Heteronuclear Multiple Quantum Correlation (HMQC), Heteronuclear Multiple Bond Correlation (HMBC), long-range Heteronuclear Chemical Shift Correlation (HETCOR), and Rotating-frame Overhauser Enhancement Spectroscopy (ROESY), provided molecular structure information. Mass spectra (MS) were recorded on a Kratos MS-50 in high resolution power electron impact scanning mode, 70 ev. Resolution was set to 2000, scanning rate 10 sec/decay, temperature gradient from 50° to 300° C. increased at a rate of 50°/min. IR spectra were recorded on a Perkin-Elmer 1600 Series FTIR. UV spectra were recorded on a Perkin-Elmer Lambda 2 UV/VIS spectrometer or taken directly from the Hitachi diode-array UV detector on the HPLC system. Melting points were measured on a Buchi 535 apparatus and are uncorrected.

6.2 Isolation of Epicacalone, Cacalone and Compound 3 Using an Aqueous and Alcoholic Solvent Extraction In a general scheme for the isolation of bioactive compounds from *P. decompositum*, 500 g of the shredded and ground roots of *P. decompositum* were steeped in water at a temperature of 55° C. for 24 hrs. The liquid, upon cooling, was separated from the solids by filtration. The water extract was concentrated by removal of water in vacuo to yield 77.4 g of an amorphous extract. A 15.1 g portion of this extract was treated with 90 mL of cold water followed by the addition of 600 mL of isopropyl alcohol. The mixture was left to stand at 4° C. for 12 hrs, and the solids removed by decantation. Upon separation, the supernatant was concentrated in vacuo to yield 6.45 g of an enriched bioactive mixture. A 5.53 g portion of the enriched bioactive material was then partitioned between 75 mL of dichloromethane and 55 mL of 1 N hydrochloric acid. The aqueous acidic phase was extracted three times with 75 mL of dichloromethane. The dichloromethane extracts were combined and washed three times with 50 mL of 0.5 N hydrochloric acid, and then washed twice with 100 mL of water until the aqueous phase was pH 7. The resultant dichloromethane fraction was now highly enriched in furanoeremophilane-type compounds and devoid of alkaloids. The fraction devoid of alkaloids was concentrated to dryness in vacuo to yield 163 mg. A representation of this extraction is shown in Scheme 1. This procedure was repeated in order to produce additional amounts of the enriched fraction containing the furanoeremophilane-type compounds. A 132 mg portion of the furanoeremophilane-type enriched fraction was further purified by high performance liquid chromatography using a PRP-1 (Hamilton) 20×250 mm (10 µm) column, eluting with a linear gradient of acetonitrile and water. A flow rate of 16 mL/min was used and detection of eluting peaks was performed using an UV detector at 228 nm. The chromatogram displayed one peak eluting at approximately 14.3 min. This peak was collected to yield 34 mg of enriched bioactive material. Further fractionation was accomplished using high performance liquid chromatography using an ODS-AQ (YMC Inc.) 20×200 (5 µm) column, eluting with a linear gradient of acetonitrile-water, at a flow rate of 12 mL/min. Three components were isolated and identified as epicacalone (15.2 mg), cacalone (0.6 mg), and compound 3 (2.3 mg). Compound 3 is a 1:1 mixture of two new epimeric eremophilanolide sesquiterpenes 3a and 3b.

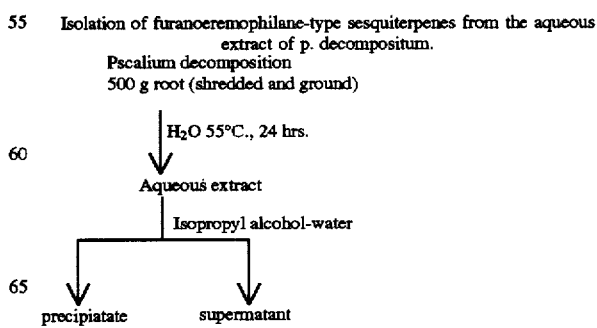

Scheme 1.

Isolation of furanoeremophilane-type sesquiterpenes from the aqueous extract of p. decompositum.

-continued
Scheme 1.

Isolation of furanoeremophilane-type sesquiterpenes from the aqueous extract of p. decompositum.

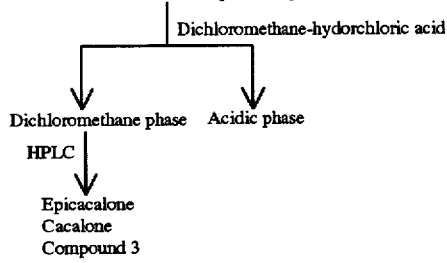

6.3 Isolation of Cacalol, Dimaturin, Compound 3, Epicacalone and Cacalone using a Non-Polar Organic Solvent Extraction Non-polar organic solvents, such as dichloromethane or mixtures of diethyl ether and hexane (1:2), can be used in the extraction process and were found to extract the furanoeremophilane-type sesquiterpenes but not pyrrolizidine alkaloids from *P. decompositum*. Isolation of gram quantities of epicacalone, cacalone and compound 3 involved using dichloromethane as the extraction solvent as shown in Scheme 2. Shredded and ground root material (5 kg) was extracted with dichloromethane for six hours at room temperature yielding 321.4 g of extract after evaporation of the dichloromethane solvent. The extract was partitioned between 10% aqueous ethanol and petroleum ether. The aqueous ethanol phase yielded 149.3 g of bioactive material after evaporation. The bioactive material was fractionated by vacuum flash chromatography using the following protocol: The bioactive material was dissolved in dichloromethane and 1.5 L of silica gel (70–230 mesh, 60 A) was added. The slurry was then dried by rotary evaporation to produce a silica gel coated with the bioactive material. The coated silica gel was added on top of 1 L of clean silica gel in a 3 L (15.5 cm i.d.) vacuum funnel for a final bed size of 15.5×12 cm. The column was eluted with hexane and ethyl acetate. Fraction 1, eluting with hexane/ethyl acetate (85:15), contained 38.5 g of enriched material. This material was recrystallized from petroleum ether to afford 14.8 g of cacalol. Fraction 2 was obtained from the silica gel column by eluting with hexane/ethyl acetate 85/15 to 80/20. After removal of solvent this fraction gave 8.97 g. Recrystallization from ethyl acetate yielded dimaturin (0.14 g). Upon further elution with hexane/ethyl acetate (80/20) fraction 3 was obtained. This fraction (15.2 g) was purified by HPLC on a PRP-1 (Hamilton) 50×250 mm column eluting with a linear gradient of acetonitrile-water. In this manner compound 3 (1.06 g) was obtained and was a mixture of 1:1 epimers 3a and 3b. Further elution on the PRP-1 column resulted in an enriched fraction containing a mixture (~1:1:1) of epicacalone, cacalone and compound 3 (5.56 g). The mixture was further chromatographed on a Primesphere ODS HC 10μ, 50×250 mm column (Phenomenex) equipped with a precolumn (50×30 mm) under isocratic conditions (70/30 acetonitrile/water, 50 mL/min, 15 min.) to yield 1.43 g of epicacalone and 3.24 g of a mixture of cacalone and compound 3. The final separation of cacalone from compound 3 was carried out by re-chromatographing the cacalone/compound 3 mixture (8×150 mg) on the Primesphere ODS column with isocratic conditions (60/40 acetonitrile/water, 50 mL/min, run time: 25 min) to give pure cacalone (412 mg) and compound 3 (350 mg). The two epimers of compound 3 were separated by HPLC with a semi-preparative phenyl (YMC Inc.) 20×250 mm (5 μm) column with a linear gradient of methanol-water (15 mL/min, 11–12 min).

Scheme 2.

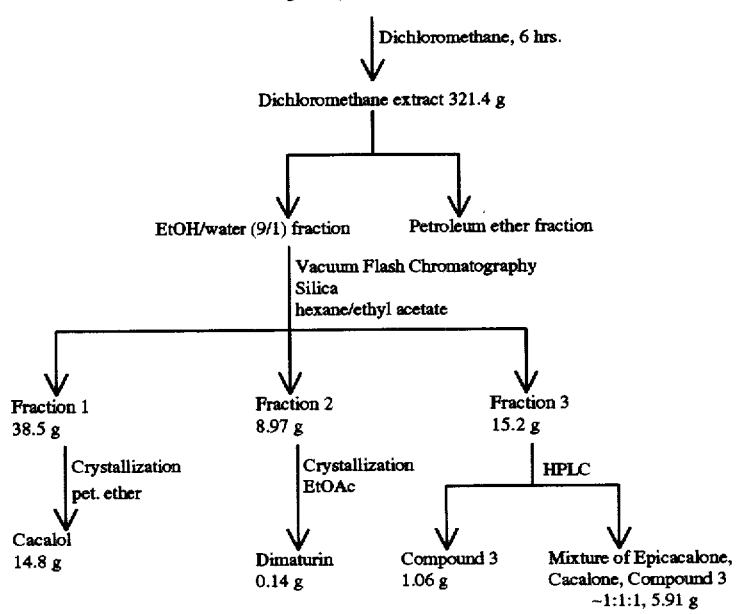

-continued
Scheme 2.

Isolation of furanoeremophilane-type sesquiterpenes from a dichloromethane extract of P. decompositum.

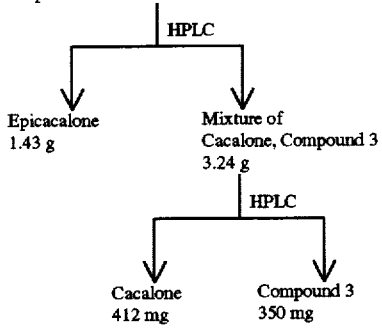

6.4 Structure Elucidation of Cacalol, Dimaturin, Compound 3, Epicacalone and Cacalone Epicacalone (1) was obtained as a white solid, m.p. 128°–130°, $[\alpha]_D$+81° (c 1.00). The IR spectrum (thin film on KBr) indicated the presence of the hydroxy (3413 $cm^{-1}$) and also showed bands at 2934 and 1652 $cm^{-1}$. The HPLC UV diode-array spectrum displayed two absorption maxima at 257 and 325 nm in acetonitrile-water (~1:1). The molecular formula, $C_{15}H_{18}O_3$, was determined by high resolution electron impact mass spectrometry (HREIMS) m/z 246.1254 ($M^+$, $\Delta$0.2 mmu of calc.) and a DEPT $^{13}$C NMR spectrum. Comparison of the reported chemical shifts for cacalone (F. Yuste, E. Diaz, F. Walls, K. Jankowski, J. Org. Chem., 1976, 41, 4103–4106; K. Jankowski, E. Diaz, F. Yuste, Proc. Indian Acad. Sci. (Chem. Sci.), 1984, 93, 1317–1321) to those assigned in epicacalone indicated similar shifts were observed overall, however several of the assignments were not in agreement. Tables 1 and 2 list the assigned $^{13}$C and $^1$H chemical shifts for epicacalone and are based on one and two-dimensional NMR experiments known to those skilled in the art of structure elucidation and include Distortionless Enhancement Polarization Transfer (DEPT), H-H Correlation Spectroscopy (COSY), Heteronuclear Multiple Quantum Correlation (HMQC), Heteronuclear Multiple Bond Correlation (HMBC), long-range Heteronuclear Chemical Shift Correlation (HETCOR) experiments.

The stereochemistry in epicacalone was assigned as 4-β-hydroxy-5-β-methyl based on the comparison of the $CH_3$-5 proton chemical shift (1.31 ppm, lit. value 1.31 ppm (K. Omura, M. Nakanishi, K. Takai, K. Naya, Chem. Letters, 1978, 1257–1260) and melting point of epicacalone isolated herein (128°–130°) with the reported values for epicacalone (lit. m.p. 129°–131° (K. Omura, M. Nakanishi, K. Takai, K. Naya, Chem. Letters, 1978, 1257–1260)). The absolute stereochemistry at C-5 in cacalone was previously established as S (M. Terabe, M. Tada, T. Takahashi, Bull. Chem. Soc. Jpn., 1978, 51, 661–662). One discrepancy was noted between the $[\alpha]_D$ values reported for epicacalone (+95°) and cacalone (+87°) with those measured for epicacalone (+81°) and cacalone (+95°) obtained from this isolation process. The values appear to be reversed. In order to ensure that the stereochemistry for epicacalone obtained from extraction of P. decompositum was the same as the epicacalone reported in the literature, ROESY experiments were performed with both epicacalone and cacalone obtained herein then compared to calculated distances of key protons from molecular modeling results with literature-reported epicacalone and cacalone. A ROESY correlation was observed between $CH_3$-3 to $CH_3$-5 in epicacalone while absent in cacalone. The relative calculated distances between protons from $CH_3$-3 to $CH_3$-5 in epicacalone and cacalone predicts these methyls to be closer in epicacalone (4.9 vs. 5.8 Å) and separated by too great a distance in cacalone for an nOe effect. In addition, a strong ROESY correlation was observed between $CH_3$-4 and $CH_3$-5 in cacalone while a weak ROESY correlation was observed in epicacalone. This correlation reflects the closer distance between protons $CH_3$-4 to $CH_3$-5 in cacalone (2.2 Å). The ROESY correlations and modeling results support the assigned stereochemistry of 1 as epicacalone and 2 as cacalone.

| Calculated distances (Å) | Cacalone | Epicacalone |
|---|---|---|
| $CH_3$-3–$CH_3$-5 | 4.9 | 5.8 |
| $CH_3$-3–$CH_3$-4 | 2.4 | 2.4 |
| $CH_3$-4–$CH_3$-5 | 4.0 | 2.2 |

The assigned stereochemistry for epicacalone including the prochirality of H-6/H-6' and H-8/H-8' are shown below.

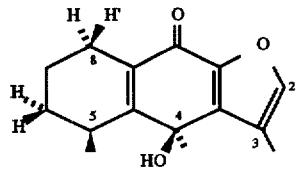

Cacalone (2) was obtained as a white solid, m.p. 139°–141°, $[\alpha]_D$ +95° (c 1.00). Spectra obtained for cacalone were very similar to epicacalone. The IR spectrum (thin film on KBr) indicated the presence of the hydroxy group (3390 $cm^{-1}$) and also showed bands at 2937 and 1652 $cm^{-1}$. The HPLC UV diode-array spectrum displayed two absorption maxima at 253 and 326 nm in acetonitrile-water (~1:1). The molecular formula, $C_{15}H_{18}O_3$, was determined by HREIMS m/z 246.1251 ($M^+$, $\Delta$0.5 mmu of calc.) and a DEPT $^{13}$C NMR spectrum. COSY, HMQC and HMBC experiments were used to completely assign the $^{13}$C and $^1$H chemical shifts in cacalone which are listed in Tables 1 and 2. The stereochemistry at C-4 in cacalone was assigned as 4-α-hydroxy-5-β-methyl based on the comparison of the $CH_3$-5 proton chemical shift (1.26 ppm, lit. value 1.24 ppm (K. Omura, M. Nakanishi, K. Takai, K. Naya, Chem. Letters, 1978, 1257–1260)) and melting point of SP-67002 (139°–141°)

with the reported values (lit. m.p. 139°–141°) (K. Omura, M. Nakanishi, K. Takai, K. Naya, Chem. Letters, 1978, 1257–1260).

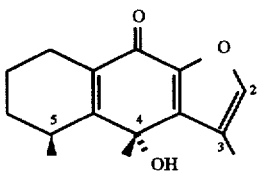

Compound 3 was obtained as a 1:1 mixture of two epimers and identified as a new eremophilanolide sesquiterpene. A single peak was displayed by HPLC with an ODS-AQ (YMC) column; however, two peaks in a 1:1 ratio were observed with a phenyl column utilizing a methanol-water gradient. A doubling of peaks was also observed in carbon and proton NMR spectra suggesting the presence of a 1:1 mixture. The IR spectrum (thin film on KBr) indicated the presence of the hydroxy (3374 cm$^{-1}$) and lactone (1798 cm$^{-1}$) and also showed bands at 2930 and 1635 cm$^{-1}$. The UV displayed two absorption maxima at 201 nm (log ε 4.27) and 295 nm (log ε 3.37). The molecular formula, $C_{15}H_{18}O_4$, was determined by HREIMS m/z 262.1204 (M$^+$, Δ0.4 mmu of calc.) and a DEPT $^{13}$C NMR spectrum. Tables 1 and 2 list the assigned $^{13}$C and $^1$H chemical shifts for compound 3 and are based on two-dimensional NMR experiments, including COSY, HMQC, HMBC, and long-range HETCOR experiments. The two epimers of compound 3 were separated by HPLC with a semi-preparative phenyl (YMC Inc.) 20×250 mm (5 μm) column with a linear gradient of methanol-water (15 mL/min, 11.2 min, 12.0 min). The stereochemistry at C-3 is described for 3a and 3b below.

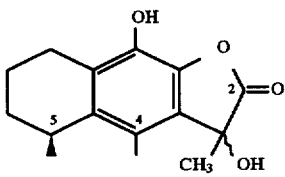

Compound 3a was obtained as a white solid, [α]$_D$+35° (c 0.462). The molecular formula, $C_{15}H_{18}O_4$, was determined by HREIMS m/z 262.1207 (M$^+$, Δ0.2 mmu of calc.) and a DEPT NMR spectrum. The carbon and proton chemical shifts in Tables 1 and 2 were assigned by analysis of COSY, HMQC, HMBC and long-range HETCOR experiments. The stereochemistry at C-3 and C-5 was assigned as 3β-hydroxy-3α-methyl and 5β-methyl and was based on ROESY and proton NMR spectra.

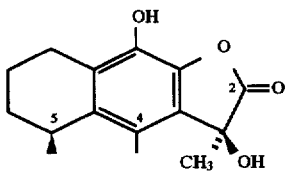

Compound 3b was obtained as a white solid, [α]$_D$–18° (c 0.588). The molecular formula, $C_{15}H_{18}O_4$, was determined by HREIMS m/z 262.1216 (M$^+$, Δ1.1 mmu of calc.) and a DEPT NMR spectrum. The carbon and proton chemical shifts in Tables 1 and 2 were assigned by analysis of COSY, HMQC, HMBC and long-range HETCOR experiments. The stereochemistry at C-3 and C-5 was assigned as 3α-hydroxy-3β-methyl and 5β-methyl and was based on ROESY and proton NMR spectra.

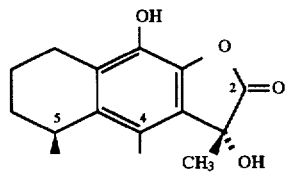

Cacalol (4) was obtained as a yellow crystalline solid after recrystallization from petroleum ether. The IR spectrum (thin film on KBr) indicated the presence of a hydroxy group (3057 cm$^{-1}$) and also exhibited bands at 2927 cm$^{-1}$ and a weak transition at 1629 cm$^{-1}$. The HPLC UV diode-array spectrum displayed two absorption maxima at 257 and 221 nm in acetonitrile-water (~1:1). The molecular formula, $C_{15}H_{18}O_2$, was determined by HREIMS m/z 230.1309 (M$^+$, Δ0.2 mmu of calc.) and a DEPT NMR spectrum. The overall $^{13}$C shifts were similar in magnitude to reported valves, however several assignments differ. COSY, HMQC, and HMBC experiments were used to accurately assign the $^{13}$C and $^1$H chemical shifts in cacalol which are listed in Tables 1 and 2, respectively.

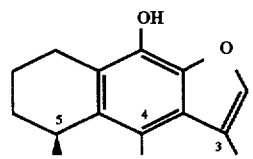

Dimaturin (5) (J. Correa, J. Romo, Tetrahedron, 1966, 22, 685–691) was obtained as a yellow solid after recrystallization in ethyl acetate or acetone, m.p. 202°–204° C. (lit. m.p. 201°–203°). A FAB MS spectrum exhibited a [M+1]$^+$ peak at 523, and is consistent with the molecular formula $C_{32}H_{26}O_7$. Analysis of the DEPT NMR spectrum indicated that there were nine unsaturated CH groups including one aldehyde, four CH$_3$'s consisting of two methoxy's and two methyls attached to an aromatic ring system, one hemiacetal, and two O—CH$_2$— groups. Comparison of the proton NMR with one reported for dimaturin, along with the DEPT data, confirmed the structure of dimaturin. $^{13}$C NMR (CDC13, 100 OMHz, δ in ppm, multiplicity): 193.4 (d), 148.8 (s), 147.8 (d), 142.4 (s), 141.7 (s), 138.8 (s), 137.6 (d), 133.4 (s), 130.7 (s), 130.3 (s), 130.1 (d), 128.2 (d), 128.0 (s), 127.8 (s), 126.0 (s), 125.2 (s), 124.5 (d), 123.3 (d), 121.7 (s), 121.5 (d), 121.2 (s), 120.9 (d), 118.5 (s), 116.7 (s), 114.2 (s), 95.7 (d), 63.0 (t), 61.0 (q), 60.2 (q), 54.5 (t), 26.6 (q), 23.3 (q). $^1$H NMR (CDC$_{13}$, 400 MHz, δ in ppm, multiplicity, J (Hz), number of hydrogens): 2.72 (s, 3H), 2.87 (s, 3H), 4.39 (s, 3H), 4.24 (s, 3H), 4.97 (d, 14, 1H), 5.08 (dd, 14, 1.2, 1H), 5.14 (dd, 14, 2.0, 1H), 5.34 (dd, 14, 1.6, 1H), 6.80 (s, 1H), 7.25 (m, 2H), 7.35 (m, 2H), 7.41 (m, 1H), 7.78 (m, 1H), 8.24 (m, 1H), 8.31 (dd, 8.4, 0.8, 1H), 10.9 (s, 1H).

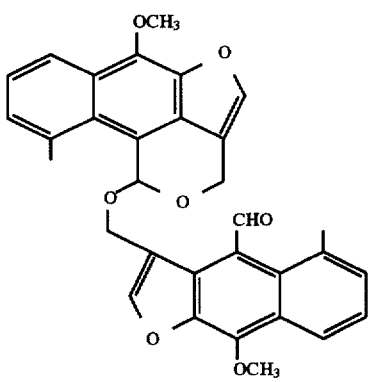

7. EXAMPLE: REDUCTION OF PLASMA GLUCOSE

7.1 Reduction of Plasma Glucose with Cacalol

This example illustrates the effectiveness of cacalol in reducing plasma glucose levels in obese diabetic ob/ob mice, i.e., an art-recognized model of non-insulin dependent diabetes mellitus (NIDDM) useful in predicting hypoglycemic activity in mammals, including humans.

7.1.1 Materials and Methods

Genetically-altered obese diabetic mice (designated C57BL/6J-ob/ob) were purchased from The Jackson Laboratory (Bar Harbor, Me, USA), and served as experimental animals. Male animals between the ages of 8–9 weeks were employed in the studies described herein. Animals were housed (4 mice/cage) under standard laboratory conditions at 22° C. and 50% relative humidity, and were maintained on

TABLE 1

$^{13}$C Chemical Shift Values for Epicacalone, Cacalone, Compound 3, Cacalol 4, Compound 3a and Compound 3b

| Carbon # | epicacalone | cacalone | Compound 3 | cacalol | Compound 3a | Compound 3b |
|---|---|---|---|---|---|---|
| 2 | 144.3 (d, $J_{C-H}$ = 202 Hz) | 144.3 d | 178.3–178.0 s | 140.7 d | 178.7 s | 178.0 s |
| 3 | 120.2 s | 120.3 s | 74.6–74.4 s | 117.0 s | 74.4 s | 74.5 s |
| 3a | 140.4 s | 140.4 s | 124.6–124.5 s | 126.0 s | 124.7 s | 124.5 s |
| 4 | 72.2 s | 70.5 s | 125.0–124.9 s | 120.1 s | 124.9 s | 124.8 s |
| 4a | 161.6 s | 161.6 s | 138.5–138.3 s | 135.5 s | 138.2 s | 138.5 s |
| 5 | 28.5 d | 27.2 d | 28.7–28.6 d | 28.9 d | 28.7 d | 28.6 d |
| 6 | 30.2 t | 30.1 t | 29.6–29.4 t | 30.0 t | 29.6 t | 29.4 t |
| 7 | 16.0 t | 15.6 t | 16.2–16.1 t | 16.6 t | 16.2 t | 16.1 t |
| 8 | 21.6 t | 20.7 t | 23.0–23.2 t | 22.9 t | 23.2 t | 23.0 t |
| 8a | 130.6 s | 130.6 s | 126.65–126.59 s | 118.7 s | 126.6 s | 126.6 s |
| 9 | 175.0 s | 175.1 s | 135.4–135.1 s | 136.2 s | 134.9 s | 135.5 s |
| 9a | 145.1 s | 145.2 s | 137.0–136.8 s | 142.1 s | 137.0 s | 136.8 s |
| $CH_3$-3 | 8.8 q | 9.0 q | 24.6–24.1 q | 11.2 q | 24.0 q | 24.6 q |
| $CH_3$-4 | 27.2 q | 25.7 q | 12.64–12.61 q | 13.7 q | 12.6 q | 12.6 q |
| $CH_3$-5 | 21.3 q | 20.7 q | 20.75–20.72 q | 21.3 q | 20.7 q | 20.8 q |

TABLE 2

$^{1}$H Chemical Shift Values for Epicacalone, Cacalone, Compound 3, Cacalol, Compound 3a and Compound 3b.

| Proton # | epicacalone | cacalone | Compound 3 | cacalol | Compound 3a | Compound 3b |
|---|---|---|---|---|---|---|
| 2 | 7.34 (1H, q, 1.2) | 7.31 (1H, m) | | 7.27 (1H, s) | | |
| 5 | 2.87 (1H, m) | 3.12 (1H, m) | 3.04 (2H, m) | 3.28 (1H, m) | 2.95 (1H, m) | 3.01 (1H, m) |
| 6 | 1.58 (1H, dddd, 12, 12, 4, 4) | 1.47 (1H, dddd, 13, 13, 4, 4) | 1.6 (2H, m) | 1.84 (2H, m) | 1.52 (1H, m) | 1.7 (2H, m) |
| 6' | | | 1.76 (2H, m) | | 1.7 (1H, m)[2] | |
| | 1.70 (1H, m) | 1.68 (1H, m) | | | | |
| 7 | 1.75–1.8 (2H, m) | 1.72 (1H, m) | 1.8 (4H, m) | 1.9 (2H, m) | 1.7 (2H, m)[2] | 1.77 (2H, m) |
| 7' | | 1.83 (1H, m) | | | | |
| 8 | 2.33 (1H, ddd, 18, −9, −9) | 2.35 (1H, dd, 19.6, 8.8)[1] | 2.49 (1H, broad, dd) 2.34 (1H, m) | 2.68 (1H, ddd, 18, 11.2, 6.8) | 2.24 (1H, dd?, 18, 8.8)[3] | 2.45 (1H, ddd, 18, 10, 8) |
| 8' | | 2.54 (1H, ddd, 19, 8.4, 2.8) | 2.84/2.8 (2H, m) | | 2.75 (1H, broad d, 18) | |
| | 2.54 (1H, ddd, 18, 6.8, 2.4) | | | 3.04 (1H, ddd, 17.2, 5.2, 1.2) | | 2.83 (1H, broad dd, 18, 6) |
| $CH_3$-3 | 2.23 (3H, d, 1.2) | 2.23 (3H, d, 1.2) | 1.73 (3H, s) 1.74 (3H, s) | 2.42 (3H, s) | 1.67 (3H, s) | 1.69 (3H, s) |
| $CH_3$-4 | 1.67 (3H, s) | 1.68 (3H, s) | 2.334 (3H, s) 2.326 (3H, s) | 2.56 (3H, s) | 2.28 (3H, s) | 2.29 (3H, s) |
| $CH_3$-5 | 1.31 (3H, d, 7.2) | | 1.12 (3H, d, 7.2) 1.14 (3H, d, 7.2) | 1.24 (3H, d, 7.2) | 1.05 (3H, d, 7.2) | 1.10 (3H, d, 6.8) |

[1]Slight overlap between H-8 and H-8', multiplicity may be ddd as in epicacalone
[2]Overlap with H-6 and H-7
[3]Slight overlap with $CH_3$-4, multiplicity could be ddd.

a diet of Purina rodent chow and water ad libitum. Prior to treatment, blood was collected from the tail vein of each animal. Mice that had plasma glucose levels between 250 and 500 mg/dL were used. Each treatment group consisted of eight mice that were distributed so that the mean glucose levels were equivalent in each group at the start of the study. Diabetic ob/ob mice were dosed orally by gavage once each day for two days with either vehicle, cacalol, administered at 125 mg (544 µmol), 250 mg (1088 µmol), or 500 mg (2176 µmol/kg/day], or metformin [250 mg (1510 µmol)/kg/day]. Compounds were delivered in a liquid vehicle containing 0.25% (w/v) carboxymethylcellulose, 1% (v/v) Tween 60, and up to 10% (v/v) dimethyl sulfoxide (DMSO) in a volume of 10 ml/kg. Blood was sampled from the tail vein three hours post-dosing, and analyzed for plasma glucose levels. Individual body weights and mean food consumption (each cage) were also measured after 24 h. Cacalol was purified as described in Section 6.3, above. Metformin (1,1-dimethylbiguanide) was purchased from Sigma Chemical Co. (St. Louis, Mo, USA; catalog# D-5035). Plasma glucose levels were determined colorimetrically using glucose oxidase (Sigma Chemical Co.; Sigma catalog# 315). Significant differences between groups (comparing drug-treated to vehicle-treated) were evaluated using analysis of variance and Fisher's post-hoc test.

7.1.2 Results

As illustrated in FIG. 1, metformin (reference compound) and all three dose-levels of cacalol resulted in significant reductions in plasma glucose at both dose intervals with changes in 68, 77, and 94 mg/dL in the 544 µmol, 1088 µmol, or 2176 µmol/kg groups after the second dose (P<0.0243, 0.007, and 0.003, respectively). The antihyperglycemic effects of cacalol at 544 µmol/kg and 1088 µmol/kg occurred in the absence of any measurable effect on food intake or body weight (Table 3). When given at 2176 µmol/kg, cacalol did result in a reduction in food intake. Metformin (1510 µmol/kg) lowered plasma glucose by approximately 108 mg/dl 3 hours after the initial dose (P<0.0001), and by approximately 80 mg/dl 3 hours after the second dose (P<0.0001). These data indicate that cacalol is an effective oral anti-hyperglycemic agent in a rodent model of insulin resistance, obesity, and NIDDM.

TABLE 3

Effect of Cacalol on Body Weight and Food Consumption

| TREATMENT | Body weight (g/mouse) (mean ± sem) 0 h | Body weight (g/mouse) (mean ± sem) 24 hr | Food Intake (g/mouse) 0–24 hr |
|---|---|---|---|
| Vehicle | 45.1 ± 0.9 | 45.2 ± 1.0 | 5.3 |
| Metformin 250 mg/kg | 47.2 ± 0.9 | 47.5 ± 0.9 | 5.0 |
| Cacalol 125 mg/kg | 49.7 ± 1.2 | 49.5 ± 1.2 | 5.2 |
| Cacalol 250 mg/kg | 47.2 ± 0.7 | 47.4 ± 0.9 | 4.7 |
| Cacalol 500 mg/kg | 45.9 ± 0.8 | 44.5 ± 1.1 | 2.1 |

7.2 Reduction of Plasma Glucose with Epicacalone, Cacalone and Compound 3

This example illustrates the beneficial effects of the pure compounds epicacalone, cacalone, compound 3 and cacalol in reducing plasma glucose levels in obese diabetic ob/ob mice.

7.2.1 Materials and Methods

Using methods more fully described in Section 7.1.1 above, diabetic ob/ob mice (8 animals/group) were dosed with single oral doses with either vehicle, epicacalone, cacalone, compound 3 or cacalol at a molar equivalent dose of 1090 µmol/kg/day, or metformin at 250 mg (1510 µmol)/kg/day. Blood was sampled from the tail vein 3 h post dosing, and analyzed for plasma glucose levels as before. Individual body weights and mean food consumption (each cage) were also measured after 24 h. Epicacalone, cacalone, compound 3 and cacalol were purified as described in Section 6.3, above.

7.2.2 Results

Figure 2:
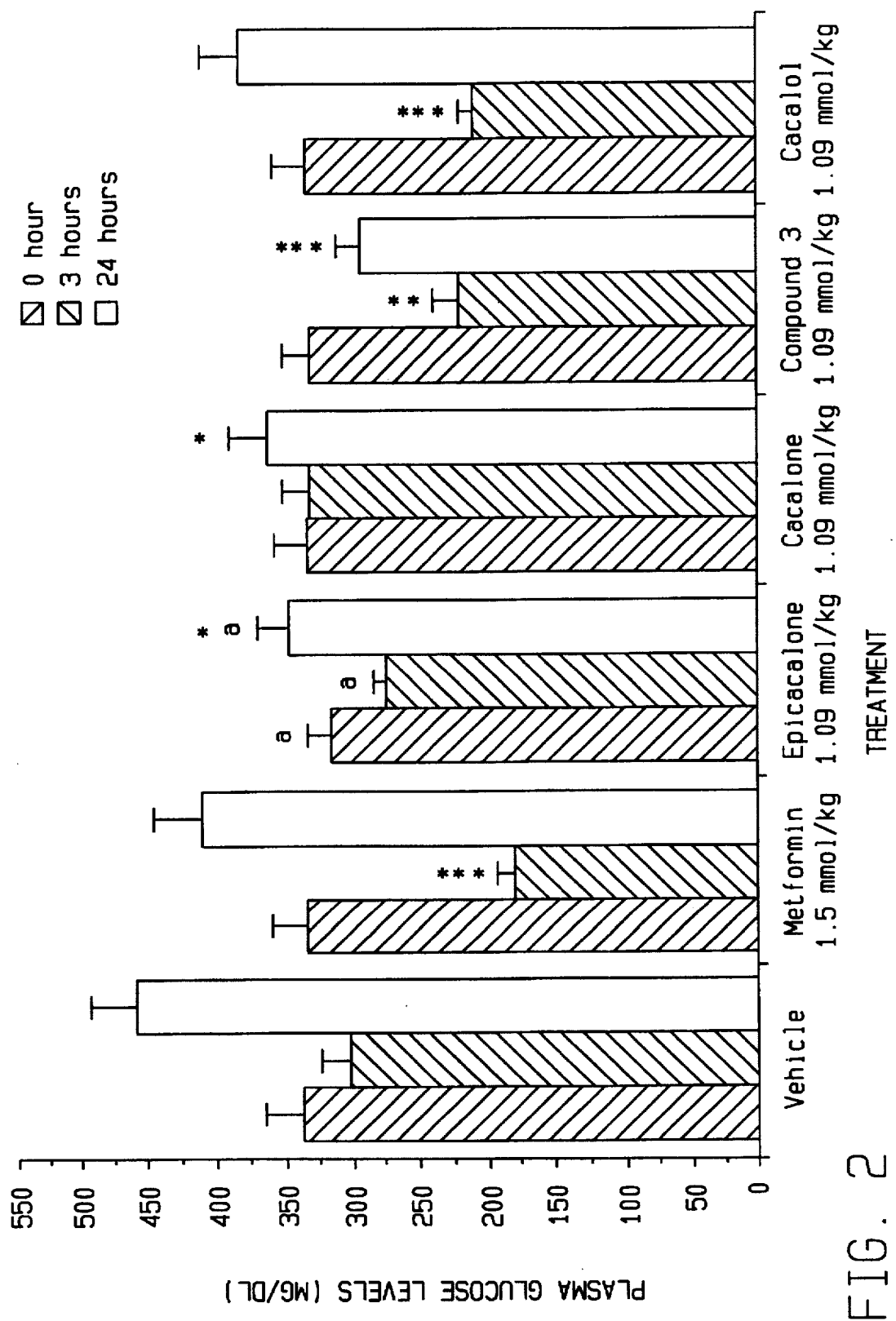

Single doses of compound 3 or cacalol (1090 µmol/kg/day/kg) given to diabetic C57B1/6J ob/ob mice resulted in significant reductions in plasma glucose relative to vehicle controls 3 h after oral administration, while all compounds resulted in a statistically significant reduction in glucose levels relative to control values by 24 h after a single dose (FIG. 2). Three hours after dosing, glucose levels declined 110 and 124 mg/dL for compound 3 (P<0.0016) and cacalol (P<0.0005), respectively, from the baseline values. By comparison, the known hypoglycemic agent metformin caused a reduction in plasma glucose levels of 152 mg/dL (P<0.0001). Over the 3 h test period, there was a reduction in plasma glucose levels in vehicle controls of 35 mg/dL, a value that was not statistically significant. Body weights and food consumption were not adversely affected for any treatment groups during the test period (Table 4). Although epicacalone and cacalone did not result in substantial reductions in plasma glucose by the 3 h time period under the conditions of this experiment, epicacalone and cacalone do result in increased glucose transport in vitro; an art recognized in vitro system that represents an important mode of action for glucose utilization and disposal in mammals. Additionally, it would be recognized by those skilled in the art that under the conditions in which these compounds were evaluated in vivo, i.e., a single dose, differences in pharmacokinetics, absorption, or pharmacology could explain the reduced activity compared to compound 3 and cacalol.

TABLE 4

Effect of Epicacalone, Cacalone, Compound 3, and Cacalol on Body Weight and Food Consumption

| TREATMENT | Body weight (g/mouse) (mean ± sem) 0 h | Body weight (g/mouse) (mean ± sem) 24 hr | Food Intake (g/mouse) 0–24 hr |
|---|---|---|---|
| Vehicle | 44.1 ± 0.8 | 44.1 ± 0.8 | 5.1 |
| Metformin 250 mg/kg | 43.5 ± 0.4 | 43.2 ± 0.5 | 4.5 |
| Epicacalone 267 mg/kg | 44.1 ± 1.6 | 43.3 ± 1.5 | 4.0 |
| Cacalone 267 mg/kg | 41.6 ± 0.9 | 41.4 ± 0.9 | 4.8 |
| Compound 3 285 mg/kg | 42.9 ± 1.2 | 42.6 ± 1.2 | 4.8 |
| Cacalol 250 mg/kg | 44.1 ± 0.8 | 43.5 ± 0.7 | 4.1 |

7.3 Reduction of Plasma Glucose with Dimaturin

This example illustrates the beneficial effects of pure compound dimaturin in reducing plasma glucose levels in obese diabetic ob/ob mice.

7.3.1 Materials and Methods

Using methods more fully described in Section 7.1.1 above, diabetic ob/ob mice (8 animals/group) were dosed with single oral doses with either vehicle, dimaturin at doses of 250 mg (0.48 mmol)/kg/day, or metformin at 250 mg (1.51 mmol)/kg/day. Blood was sampled from the tail vein 3 h post dosing, and analyzed for plasma glucose levels as before. Individual body weights and mean food consumption (each cage) were also measured after 24 h. Dimaturin was purified as described previously in Section 6.3.

7.3.2. Results

Figure 3:
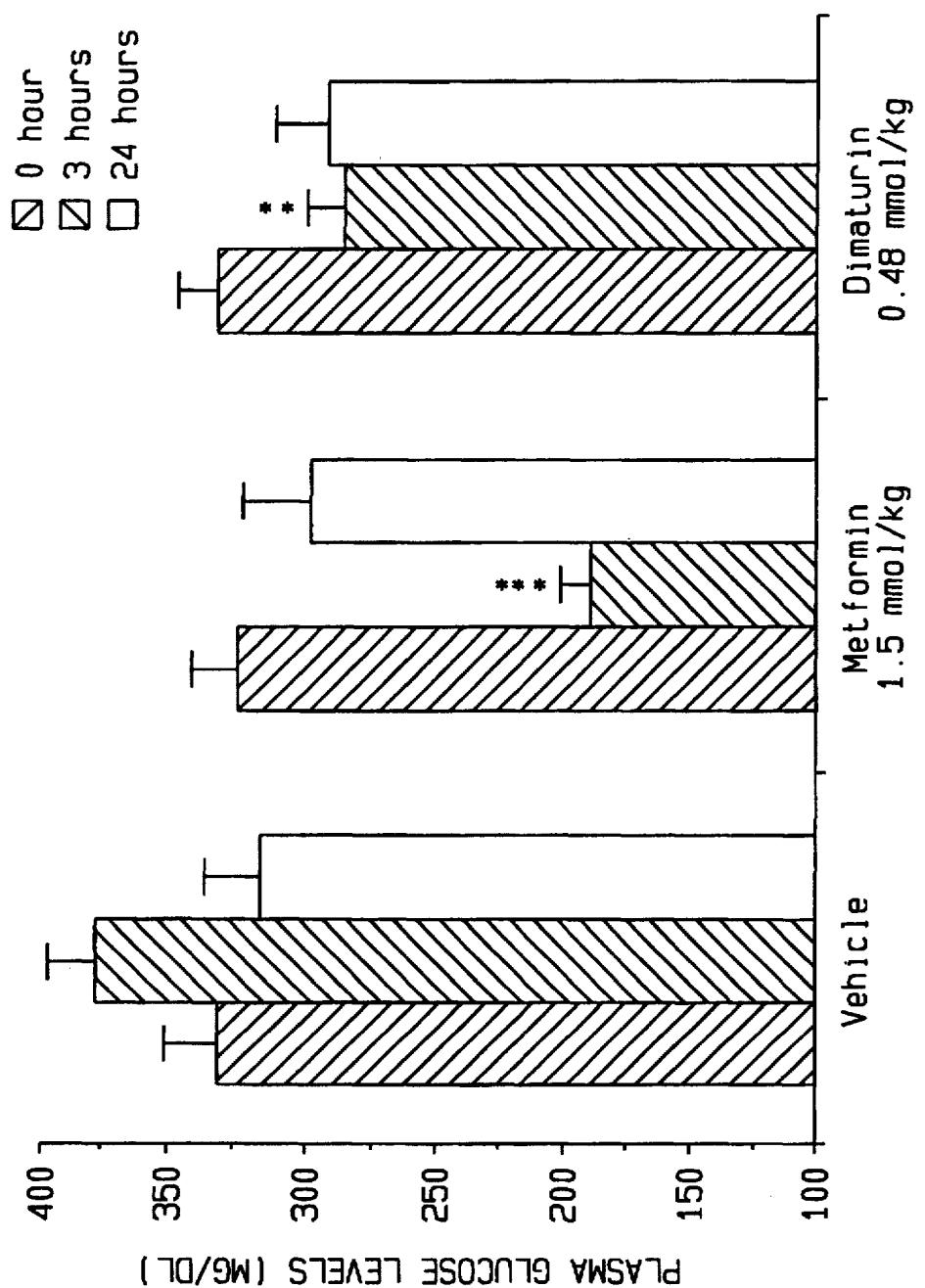
FIG. 3 is a bar graph showing the plasma glucose levels (mg/dl) of diabetic mice treated with dimaturin. $P<0.01$; $*P<0.001$ (ANOVA, one factor).

As illustrated in FIG. 3, a single dose of dimaturin given to diabetic C57Bl/6J ob/ob mice given at a level of 0.48 mmol/kg resulted in significant reductions in plasma glucose relative to vehicle controls 3 h after oral administration, while glucose levels returned to baseline values by 24 h. Three hours after dosing, glucose levels declined 45 mg/dL for dimaturin (p=0.0031) from the baseline value. By comparison, the known hypoglycemic agent metformin caused a reduction in plasma glucose levels of 135 mg/dL (p<0.0001). Over the 3 h test period, there was an increase in plasma glucose levels in vehicle controls of 45 mg/dL, a value that is not statistically significant. Body weights and food consumption were not adversely affected for any treatment groups during the test period.

These data indicate that dimaturin is an effective oral anti-hyperglycemic agent in a rodent model of insulin resistance, obesity, and NIDDM.

8. EXAMPLE: STIMULATION OF GLUCOSE TRANSPORT

This example illustrates the ability of epicacalone and cacalone to directly stimulate glucose transport in 3T3-L1 adipocytes, an art recognized in vitro system that represents an important mode of action for glucose utilization and disposal (i.e., transfer of plasma glucose to surrounding tissues) in mammals. Metformin, a drug that enhances glucose disposal and one that is currently used to treat NIDDM, exhibits significant stimulatory activity in this model system.

8.1 Materials and Methods

Murine 3T3-L1 preadipocytes (American Type Culture Collection CL 173) were maintained in Dulbecco's modified Eagles medium (DMEM) containing 10% (v/v) supplemented calf serum, antibiotics, and 25 mM glucose. Cells were seeded in 24-well cluster plates (10,000 cells/well), grown to confluence (typically 5 days), and induced to differentiate 2 days post-confluence (day 0) according to the standard protocol of Frost and Lane [Frost, S. and Lane, M.D. (1985) J. Biol. Chem. 260, 2646-2652]. Following differentiation, adipocytes were maintained in DMEM containing 10% fetal bovine serum, and provided with fresh medium every 2-3 days. Adipocytes employed in this study were used on days 7-10 post-differentiation. On the day of the experiment, adipocytes were washed with phosphate-buffered saline and switched to serum-free DMEM medium. Adipocytes were treated (in triplicate) for 18 hr with the indicated concentrations of epicacalone, cacalone, or metformin. Concentrated stock solutions of epicacalone and cacalone were freshly prepared in dimethyl sulfoxide (DMSO) and diluted into culture medium. The final concentration of DMSO was 0.2% (v/v) which was also included in basal conditions. Metformin was dissolved directly into culture medium and further diluted into the same medium. Following overnight (18 hr) treatment, the culture medium was aspirated and the monolayers washed with Krebs-Ringer Hepes buffer. To assess the effects of the compounds on basal glucose transport, 2-deoxy-D-glucose uptake (an indicator of glucose transport) was measured in the absence of insulin stimulation. To determine if 18 hr exposure to compounds potentiated the stimulatory effect of insulin, adipocytes were further treated with 0.5 nM insulin (a sub-maximal concentration) for 30 minutes at 37° C. Under these assay conditions, 0.5 nM insulin stimulates glucose transport by approximately 200-400% over basal (typically 50 nmoles 2-deoxyglucose/10 minutes/well), and 100 nM insulin (a maximally effective concentration) stimulates glucose transport by approximately 1500-2000% over basal. Glucose transport assays were initiated by the addition of 2-deoxy-D-[$^3$H]glucose (0.5 μCi/ml; 100 μM final concentrations) to each well followed by incubation for 10 min at 22° C. Assays were terminated by aspirating the media and rapidly washing the monolayer two times with ice-cold phosphate-buffered saline solution. Cell monolayers were solubilized in 0.1N NaOH, transferred to scintillation vials, and radioactivity determined by liquid scintillation counting. All data were corrected for non-specific hexose uptake determined in parallel samples treated for 5 minutes with 200 μM cytochalasin B.

8.2 Results

Figure 4:
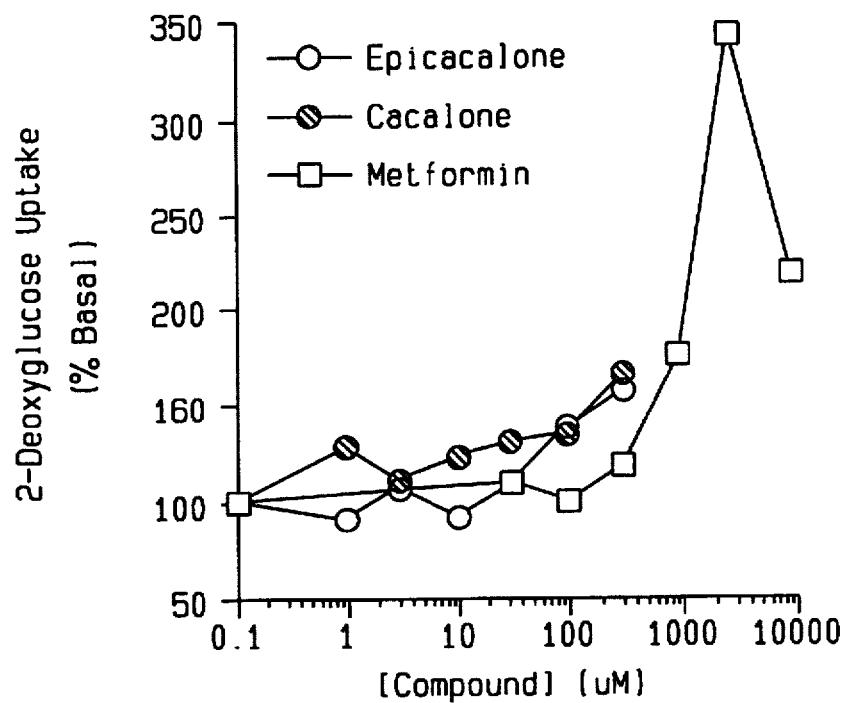
FIG. 4 is a graph showing the effects of epicacalone and cacalone on basal 2-deoxyglucose uptake in 3T3-L1 adipocytes.
Figure 5:
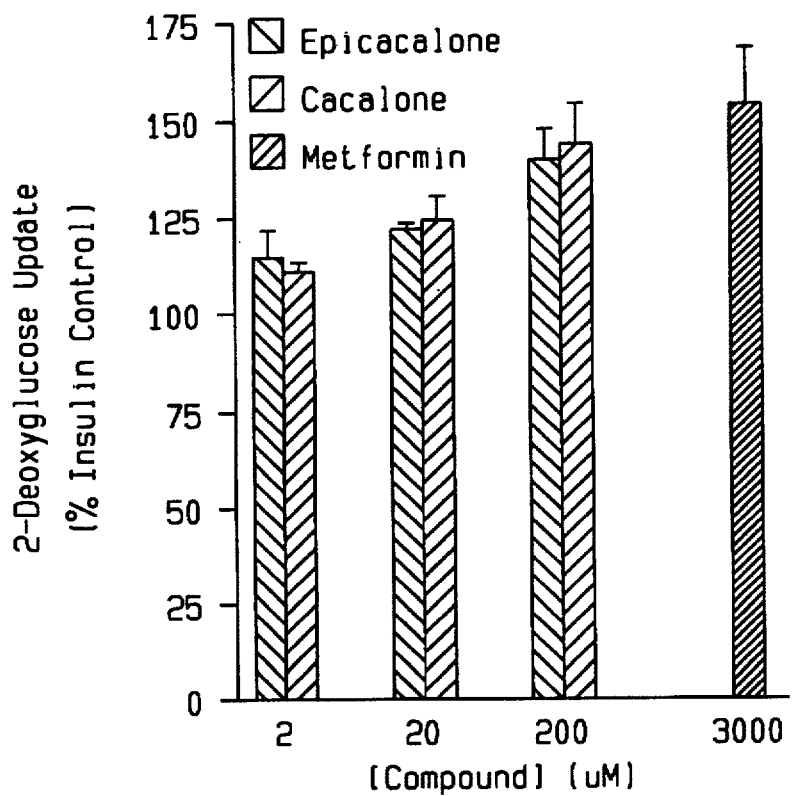
FIG. 5 is a bar graph showing the effects of epicacalone and cacalone on insulin-stimulated 2-deoxyglucose uptake in 3T3-L1 adipocytes.

Epicacalone and cacalone (100 and 300 μM) increased the rate of basal glucose transport (i.e. no added insulin) in 3T3-L1 adipocytes by approximately 50% (FIG. 4). These compounds were approximately 10 times more potent than metformin, although the magnitude of stimulation in response to metformin was greater (approximately 350% of basal). Epicacalone and cacalone (2-200 μM) also sensitized the glucose transport system in adipocytes to subsequent stimulation with a sub-maximal concentration of insulin (0.5 nM). Epicacalone and cacalone potentiated glucose transport in response to insulin by approximately 50% at 200 μM (FIG. 5). The sensitizing effects of epicacalone and cacalone were equivalent in magnitude to those elicited by metformin and were observed at substantially lower concentrations (compared to metformin), further demonstrating the enhanced potency of both epicacalone and cacalone. As would be recognized by those skilled in the art, these data indicate that epicacalone and cacalone directly stimulate glucose transport in vitro, an effect that is predicted to result in enhanced glucose disposal and glucose reduction in vivo.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited and the entire disclosures of which are incorporated herein by reference.

What is claimed is:

1. A method for reducing the blood glucose of a mammal, comprising administering to said mammal a hypoglycemically effective amount of a composition comprising an isolated or a purified compound selected from the group consisting of epicacalone, cacalone, compound 3, cacalol, dimaturin and pharmaceutically acceptable salts thereof; and a physiologically acceptable carrier.

2. The method of claim 1, wherein the pharmaceutically acceptable salt is selected from the group consisting of sodium, potassium, lithium, calcium, magnesium, zinc and iron.

3. A method for treatment of diabetes mellitus, comprising administering, to a mammal suffering from diabetes mellitus, a therapeutically effective amount of a composition comprising an isolated or a purified compound selected from the group consisting of epicacalone, cacalone, compound 3, cacalol, dimaturin and pharmaceutically acceptable salts thereof; and a Physiologically acceptable carrier.

4. The method of claim 3, wherein the pharmaceutically acceptable salt is selected from the group consisting of sodium, potassium, lithium, calcium, magnesium, zinc and iron.

5. The method of claim 3, wherein the composition is administered in conjunction with another hypoglycemic agent selected from the group consisting of a sulfonylurea, a biguanide, a thiazolidinedione, a $\beta_3$-adrenoceptor agonist, an α-glycosidase inhibitor and insulin.

6. The method of claim 5, wherein the sulfonylurea is selected from the group consisting of acetohexamide, chlorpropamide, tolazamide, tolbutamide, glyburide, glypizide and glycazide.

7. The method of claim 5, wherein the biguanide is metformin or buformin.

8. The method of claim 5, wherein the α-glucosidase inhibitor is acarbose or miglatol.

9. The method of claim 5, wherein the thiazolidinedione is troglitazone.

10. A pharmaceutical composition for use as a hypoglycemic agent in mammals, comprising a therapeutically effective amount of an isolated or a purified compound selected from the group consisting of epicacalone, cacalone, compound 3, cacalol, dimaturin and pharmaceutically acceptable salts thereof; and a physiologically acceptable carrier.

11. The pharmaceutical composition of claim 10, wherein the pharmaceutically acceptable salt is selected from the group consisting of sodium, potassium, lithium, calcium, magnesium, zinc and iron.

12. A pharmaceutical composition for use as a hypoglycemic agent in mammals, comprising a therapeutically effective amount of isolated or purified compound 3 or a pharmaceutically acceptable salt thereof, and a physiologically acceptable carrier.

13. The pharmaceutical composition of claim 12, wherein the pharmaceutically acceptable salt is selected from the group consisting of sodium, potassium, lithium, calcium, magnesium, zinc and iron.

* * * * *